United States Patent
Bhardwaj

(10) Patent No.: US 7,141,504 B1
(45) Date of Patent: Nov. 28, 2006

(54) METHOD AND APPARATUS FOR ANISOTROPIC ETCHING

(75) Inventor: Jyoti Kiron Bhardwaj, Bristol (GB)

(73) Assignee: Surface Technology Systems PLC, Gwent (GB)

( * ) Notice: Subject to any disclaimer, the term of this patent is extended or adjusted under 35 U.S.C. 154(b) by 0 days.

(21) Appl. No.: 09/744,212

(22) PCT Filed: Jul. 23, 1999

(86) PCT No.: PCT/GB99/02368

§ 371 (c)(1),
(2), (4) Date: Mar. 7, 2001

(87) PCT Pub. No.: WO00/05749

PCT Pub. Date: Feb. 3, 2000

(30) Foreign Application Priority Data

| Jul. 23, 1998 | (GB) | 9815931.2 |
| Oct. 27, 1998 | (GB) | 9823364.6 |
| Mar. 4, 1999 | (GB) | 9904925.6 |
| May 11, 1999 | (GB) | 9910725.2 |
| May 18, 1999 | (GB) | 9911401.9 |

(51) Int. Cl.
*H01L 21/461* (2006.01)
*H01L 21/302* (2006.01)

(52) U.S. Cl. ............ 438/700; 438/706; 438/719

(58) Field of Classification Search ............ 438/22, 438/694, 695, 706, 710, 712, 714, 718, 719, 438/745
See application file for complete search history.

(56) References Cited

U.S. PATENT DOCUMENTS

| 3,776,187 A | * | 12/1973 | Probst | 118/626 |
| 4,264,641 A | * | 4/1981 | Mahoney et al. | 427/30 |
| 4,529,475 A | | 7/1985 | Okano et al. | 156/643 |
| 4,579,623 A | | 4/1986 | Suzuki et al. | 165/626 |
| 4,748,043 A | * | 5/1988 | Seaver et al. | 118/638 |
| 4,749,440 A | | 6/1988 | Blackwood et al. | 156/646 |
| 4,857,142 A | | 8/1989 | Syverson | 156/646 |
| 5,213,621 A | | 5/1993 | Ivankovits et al. | 134/3 |
| 5,213,622 A | | 5/1993 | Bohling et al. | 134/3 |
| 5,221,366 A | | 6/1993 | Roberts et al. | 148/22 |
| 5,222,663 A | * | 6/1993 | Noakes et al. | 239/3 |
| 5,223,226 A | * | 6/1993 | Wittmer et al. | 422/100 |
| 5,344,676 A | * | 9/1994 | Kim et al. | 427/468 |

(Continued)

FOREIGN PATENT DOCUMENTS

DE 4317274 A1 12/1994

(Continued)

OTHER PUBLICATIONS

Butterbaugh et al., "Gas-Phase Etching of Silicon Oxide with Anhydrous HF and Isopropanol," Proceedings Electrochemical Soc. PV 1994, pp. 374-383.

(Continued)

*Primary Examiner*—Duy-Vu N Deo
(74) *Attorney, Agent, or Firm*—Volentine Francos & Whitt, PLLC

(57) ABSTRACT

There is disclosed a method of treating a substrate material or a film present on the material surface comprising cyclically performing the following steps: (a) etching the material or film; (b) depositing or forming a passivation layer on the surfaces of an etched feature; and (c) selectively removing the passivation layer from the etched feature in order that the etching proceeds in a direction substantially perpendicular to the material or film surface. At least one of the steps (a) or (b) is performed in the absence of a plasma. Also disclosed is an apparatus for performing the method.

26 Claims, 6 Drawing Sheets

U.S. PATENT DOCUMENTS 5,501,893 A * 3/1996 Laermer et al. .............. 216/67

FOREIGN PATENT DOCUMENTS

DE 19704454 A1 8/1998
WO WO 94/14187 6/1994

OTHER PUBLICATIONS

K. Torek et al., "Reduced Pressure etching of Thermal Oxides in Anhyudrous HF/Alcoholic Gas Mixtures," J. Electrochem. Soc., vol. 142, No. 4, Apr. 1995, pp. 1322-1326.

M. Wong et al., "Silicon Etch Using Vapor Phase HF/F2O and O3," J. Electrochem. Soc., vol. 140, No. 2, Feb. 1993, pp. 567-570.

Chun Su Lee et al., "Modeling and Characterization of Gas-Phase Etching of Thermal Oxide and TEOS Oxide Using Anhydrous HF and CH3OH," J. Electrochem. Soc., vol. 143, No. 3, Mar. 1996, pp. 1099-1103.

Kirt R. Williams et al., "Etch Rates for Micromachining Processing," Journal of Microelectromechanical Systems, vol. 5, No. 4, Dec. 1996, pp. 256-269.

Gregory T. A. Kovacs et al., "Bulk Micromachining of Silicon," Proceedings of the IEEE, vol. 86, No. 8, Aug. 1998, pp. 1536-1551.

C. Rinn Cleavelin et al., "Silicon Dioxide Removal in Anhydrous HF Gas," Nov. 1987, Semiconductor International, pp. 95-99.

D.L. Flamm et al., "Plasma etching," Chemistry of the Semiconductor Industry, pp. 343-390.

* cited by examiner

METHOD AND APPARATUS FOR ANISOTROPIC ETCHING

This invention relates to a method and apparatus for etching a substrate in an anisotropic manner. In particular, although not exclusively, the method and apparatus relate to treatment of a semiconductor wafer.

A method of anisotropically etching silicon by cyclic etch and deposition in a plasma environment is known from U.S. Pat. No. 4,579,623 and WO-A-9414187. This anisotropic plasma etch method has been applied to other materials such as Ge, SiGe and GaAs, to result in high etch rates (relative to conventional plasma etching where the anisotropy is controlled by simultaneous etching and passivation during the process).

Proceedings of the IEEE, 1998, Vol. 86, No.8, pp 1536–1551 discloses bulk silicon etching techniques applied in the fabrication of micromachined sensors, actuators, and structures. The available etching methods fall into three categories in terms of state of the etchant: wet, vapour and plasma. Journal of Microelectromechanical Systems, 1996, Vol.5, No.4, pp 256–269 discloses the etch rate for various materials used in the fabrication of microelectromechanical systems and integrated circuits in a variety of wet, plasma, and gas-phase etches and details of etch preparation, use and chemical reactions are given. Journal of the Electrochemical Society, 1993, Vol.140, No.2, pp 567–570 discloses gas phase etching of single and polycrystalline silicon using a mixture of $HF/H_2O$ and $O_3$. The chemistries disclosed in each of these references can be equally well used in the present invention described below.

U.S. Pat. No. 4,529,475 discloses a dry etching apparatus which uses reactive gases and which is capable of achieving anisotropic etching without causing radiation damage to a workpiece. However, the document does not disclose a cyclic or alternating process.

It is hypothesised that, in accordance with the present invention, in order to achieve anisotropic high rate etching, the following generic technique can be applied. Anisotropic high rate etching should be achievable when all of the following three conditions can be satisfied:
  (i) the material can be etched at high rate (i.e. readily or spontaneously forms a volatile reaction product when exposed to the etchant species)—this is irrespective of etch profile;
  (ii) a suitable passivation film can be deposited or the etched surface passivated such that the passivation film or passivated surface is preferentially etched at a lower rate by the etchant species than the material to be etched; and
  (iii) the passivation material can be selectively removed from the base (or horizontal surface of the material) allowing the etch to proceed parallel to this direction.

The above model of the invention states that where any of the three conditions cannot be satisfied, the method cannot be used to anisotropically etch any material. It should be noted that in order for the material to be etched, the etch product has to be removed from the surface. This can either be achieved by ensuring that the products are volatilized under the prevalent process conditions, or by other means including solvent rinsing. The precise method of achieving the above steps will depend on the material being etched and the most appropriate chemistry. Step (i) for example may be carried out either by means of a plasma or by means of a chemical in the gas, vapour or liquid phase. Step (ii) may either be passivation of the surface (for example when etching a metal or a semiconductor material by forming an oxide, nitride, carbide or other suitable interface which is resistant to the etching chemistry) or the deposition of a passivating film or layer. Techniques of forming a passivating interface or layer are well known to those skilled in the art. The following discussions therefore concentrate more on the deposition of a passivating film as this method will be applicable to the etching of dielectric layers as well as metals and semiconductors. So, step (ii) (hereafter referring only to the deposition of a passivation layer) may be carried out by means of a plasma or by means of energetic radiation (for example UV) enhanced polymerisation. Step (iii) also may be carried out in one of a number of ways such as by means of a plasma, or by means of collimated (directional) surface irradiation (including UV and IR which could be from a laser or other source). The apparatus details will therefore depend on which methods are used for each of the steps. Clearly it is beneficial to use compatible apparatus means for achieving the steps as the use of a single chamber apparatus (or single apparatus) is preferred as this will maximise the net etching rate as unnecessary substrate handling is avoided.

This invention allows the cyclic etch passivation technique to be used with materials that are not necessarily best etched by plasma means in that unacceptably low etch rates result. Instead the invention relies on a non-plasma etching or passivation step. Indeed, chemistries which are not compatible with plasma etching can be used. The plasma essentially results in some degree of dissociation of the precursor gases and the etch relies on some combination of the chemically active radicals with electrically charged particles to remove relatively volatile reaction products. Examples of applications of the invention include the etching of dielectrics such as silicon dioxide (for example by using HF based chemicals), semiconductors such as Si (whether doped or undoped) based on either known wet $HF/HNO_3/CH_3COOH$ chemistry or based on pure halogen compound chemistry such as $ClF_3$, $BrF_5$ and the like and conductors such as Au and Pt by using aqua regia ($HCl/HNO_3$) based chemistry. The wet solutions such as $HF/CH_3COOH/HNO_3$ and $HCl/HNO_3$ may be used in the vapour phase. In these cases, a number of methods may be used to deliver the wet solution to the substrate in vapour form. These include ultrasonic agitation or electrostatic charging to create a fine atomised spray above the substrate. It is understood that the etch rate will be limited to maximum approaching that of the rate of step (i) and hence the selection of the highest etch rate chemistry for maximising this is necessary. For example aqua regia can etch both Au and Pt at etch rates in the several tens of microns per minute, while the chemistry cited for silicon is capable of etch rates approaching 100 microns per minute, both of which are relatively high etch rates compared to plasma etching. The control of the anisotropy is then based on the limitation of the lateral etch direction by the passivation layer possibly in combination with precursor adjustment or processing conditions adjustment to achieve the same result.

In order to illustrate the invention, the example of silicon dioxide etching is used. However it is understood that while this defines the most appropriate methods for carrying out the 3 steps, other methods may also be appropriate. Indeed when etching other materials such alternative methods may be preferred. In particular, the invention may be used in silicon etching.

Deep etching of quartz, glass or silicon dioxide is useful in a range of applications eg: Micro-electro-mechanical systems (MEMS) (such as fluid channels, 'lab-on-a-chip' cavity), and opto-electronics optical waveguides defined in (doped and undoped) $SiO_2$.

The invention may be applied to anisotropic etching of oxides. Oxide in a broad sense refers to oxides of silicon, quartz, glasses, pyrex, $SiO_2$ deposited by CVD, and $SiO_2$ grown by thermal, plasma or other means where the Si surface is oxidised. The oxides may be doped or undoped. Oxides of some other materials such as Ge, for example, will also be etched in the same way.

Plasma etching of oxide is well known. Prior art such as Flamm and Mucha (Chapter on Plasma Etching in Chemistry of the Semiconductor Industry, Eds Moss and Ledwith, ISBN 0-216-92005-1, 1987) reveals that oxide etching by fluorine (predominantly in the form of fluorocarbon) chemistry results in the following reaction:

$$SiO_2 + CF_x \underrightarrow{plasma} 2SiF_4 + CO_x$$

The plasma provides energy which dissociates the $CF_x$ to liberate fluorine radicals and produce $CF_y^+$ ions. The ions are accelerated across the plasma sheath by the self bias potential and impact onto the $SiO_2$ surface. This ion bombardment is required for the anisotropic etching of the oxide. Indeed high etch rates (of the order of 1 µm/min) are only achieved using high ion energies (at least several hundred eV). High density plasma sources (eg ICP, ECR, MORI) can result in high etch rates at somewhat lower ion energies, but this energy is still large (up to a few hundred eV) relative to the conditions used for etching other materials (such as silicon) at comparable rates. Thus, ion bombardment plays a key role in the oxide etch process, determining etching rates, and influencing profile and mask selectivity. Typically, photoresist is used as the mask material and selectivity to the mask is typically less than 10:1. Selectivity to silicon (which may be the underlayer or indeed mask) is typically up to 20:1.

Oxide can also be etched isotropically in a plasma, usually in a "downstream" mode, that is either when the plasma is "decoupled" from the workpiece by means of a grounded or biased metallic plate or simply out of line of sight. Here the ion bombardment is negligible, and etching is primarily carried out by radicals generated in the plasma. Etch rates up to of the order of a micron per minute have been achieved using $NF_3$. Another well known means of isotropically etching the oxide is to use HF solution or vapour. HF solution (usually buffered with $NH_4OH$ to control reaction rates) can etch oxide at rates below a micron per minute, but control of etch parameters becomes difficult with chemical solutions in general as the aspect ratio increases.

Another known process is to use HF vapour chemistry. This is disclosed in Semiconductor International, November 1987, and U.S. Pat. Nos. 4,749,440 and 4,857,142 and DE 4317274 and DE 19704454. Here etch rates up to 2.4 µm/min have been reported. The reaction is:

$$SiO_2 + 4HF \rightarrow SiF_4 + 2H_2O$$

The reaction is initiated using $H_2O$ and indeed water vapour can be introduced with the anhydrous HF gas stream during the reaction to enhance the HF adsorption onto the wafer surface (reacting with the $SiO_2$ to form the hydroxide $Si(OH)_4$). Selectivity to either photoresist or silicon is high (much greater than 100:1). Other suitable chemistries that have been reported in the literature include alcohols (such as iso-propyl alcohol and methanol) replacing the water addition to the HF; refer to Butterbaugh (Proc. Electrochem. Soc. 1994, part 94–7), Lee (J.Electrochem. Soc. Vol.143, No.3, 1996) and Torek (J.Electrochem. Soc. Vol.142, No.4, 1995).

Considering plasma etching of oxide, condition (i) of the above model is very difficult to meet as isotropic etch rates and anisotropic etch rates are comparable (about 1 µm/min).

There is therefore a need for a method of reliably etching a substrate (for example an oxide) anisotropically, particularly deep etching an oxide. This can be achieved using the present invention.

According to a first aspect of the present invention, there is provided a method of treating a substrate material or film present on the material surface comprising cyclically performing the following steps:

(a) etching the material or film;
(b) depositing or forming a passivation layer on the surfaces of an etched feature; and
(c) selectively removing the passivation layer from the etched feature in order that the etching proceeds in a direction substantially perpendicular to the material or film surface, wherein at least one of steps (a) or (b) is performed in the absence of a plasma.

According to a further aspect of the present invention, there is provided a method of treating a substrate material or a film present on the material surface comprising cyclically performing the following steps:

(a) etching the material or film with one or more appropriate chemicals in the absence of a plasma;
(b) depositing or forming a passivation layer on the surfaces of an etched feature; and
(c) selectively removing the passivation layer from the etched feature in order that the etching proceeds in a direction substantially perpendicular to the material or film surface.

Thus, step (a) may be a chemical (non plasma) etch step. The passivation layer is typically deposited on all surfaces of the material or film.

Where the method is used for treating a film present on the material surface, the film may be thin. The material surface may have previously had a mask pattern defined on the surface.

By carrying out steps (a), (b) and (c), and then repeating the steps until the desired depth of etched feature is achieved, the method may provide a deep anisotropically etched feature in the material or film.

It should be noted that the first step in the cycle is not necessarily step (a).

The method is particularly applicable for the treatment of Si, SiGe, Ge and oxides although other materials such as the semiconductors or conductors mentioned above are equally applicable. Therefore, the substrate may be any substrate suitable for etching, for example a semiconductor wafer or a workpiece. The thin film may be a dielectric, semiconductor or conductor. In the case of the example cited, the dielectric may be silicon dioxide or any suitable oxide. Furthermore the material or thin film may be doped or undoped.

In one embodiment of the invention for etching oxides, $H_2O$ is present in step (a) where it acts as an initiator for the chemical etching. Additionally, or alternatively, $N_2$ or other inert gas may be present in step (a). The nitrogen may act as a carrier gas. Furthermore, nitrogen may be used as a purging gas to purge the apparatus between the various steps of the process. In addition, as mentioned above in relation to the prior art (which is incorporated herein by reference), alcohol may replace the water chemistry, for example in the form of iso-propyl alcohol and/or methanol. Alternatively, in another embodiment, other gas sources may be used in the etching step, including pure halogen molecular or compound (inter-halogen) chemistries such as $F_2$ or $ClF_3$ (including relevant permissible mixtures thereof) or $QR_y$ (where Q and R represent different elemental halogens) which will spontaneously etch silicon. The dry chemical etch of the silicon may be enhanced with surface irradiation. Surface irradiation in the present invention includes, but is not limited to excimer laser irradiation.

The passivation layer may be deposited using a polymer, for example one of the general formulae $C_xF_y$, $C_xH_y$, $C_xH_yF_z$, where x, y and z can be any suitable values.

The deposition of the passivation layer in step (b) may be carried out either with or without a plasma present. When a plasma is not present, any suitable non plasma means may be used, but one example is a photo-enhanced polymerisation process for the deposition of the passivation layer. A particular example is UV enhanced polymerisation. It has been found that this makes the method applicable to a very wide range of materials.

In one embodiment, $C_xF_y$ may be deposited as polymeric chains of the type $n(C_xF_y)$. When x=1 and y=2, this is PTFE. One of the preferred embodiment requirements of the passivation layer is that this should be highly selective to the etch chemistry. This indeed is the case with the HF chemistry which is infinitely selective to PTFE and hence to the $C_xF_y$ polymer used in step (b) and also to conventional organic masking materials such as photoresist.

The selective removal of the passivation layer (step(c)) may be carried out by means of a plasma. Alternative methods of surface irradiation may also be suitable. For example, thermal heating of either the front and/or back surface of the material or film may be used, resulting in thermolytic decomposition. Alternatively, the irradiation may be from a light source, for example laser, on the front of the material or film resulting in photolytic decomposition. The irradiation may be directional or collimated parallel to the direction of etch front propagation. Where a plasma is used, in one embodiment, the ion energy used in this plasma process step is greater than 10 eV, and is preferably between 10 and 100 eV. Preferably, the plasma does not spontaneously etch the passivation layer, as it is important to maintain directional etching by preferential removal from the base or horizontal surfaces of the feature being etched. The plasma may comprise a precursor gas or mixture of precursor gases. Examples of suitable plasmas comprise either inert gases (relative to the chemistry) such as argon, which will physically remove the polymer, or those gases which will physically remove the base layer with chemical enhancement such as halo- or hydro-carbons. In one embodiment, the precursor may be diluted with the material used for depositing the passivation layer, partially overlapping with the end of step (b). Alternatively, the precursor may either be, or be diluted with the etchant chemical used to etch the substrate, either wholly or at least partially overlapping with the whole of or start of step (a).

Whilst any suitable operating conditions can be applied to the process of the present invention, in a preferred embodiment the operating conditions are as follows:

Step (a) may be carried out at high or low pressures (for example from above atmospheric to several Torr) with no plasma present. The total chemical etchant flows may be in the range of fractions of an SLM to 10 s of SLM (standard liters per minute) using an appropriate carrier gas, a chemical enhancing agent and the main etch chemicals.

Step (b) may be carried out with a low pressure plasma, for example ranging from several hundred Torr down to several mTorr, with total gas flows ranging from a few tens of sccm up to 1 SLM, for example with carrier gas and the passivation precursor gas.

Step (c) may be carried out with a low pressure plasma, possibly up to several hundred Torr, but preferably less than 100 mTorr, with total gas flows in the 5–100 sccm range (for example for argon is used in the plasma).

In one embodiment, each of steps (a) to (c) is performed as a separate step with no overlap between each step. A pump-out step may be performed between any of the steps and particularly between steps (a) and (b) and/or between steps (c) and (a).

According to a further aspect of the present invention, there is provided an apparatus for performing the method described above, comprising a chamber having a chemical inlet and a chemical outlet in which is positioned a support for receiving a substrate, the apparatus further comprising means for etching a substrate material or a film present on the material surface with one or more appropriate chemicals, means for depositing a passivation layer on the surfaces of an etched feature, and means for selectively removing the passivation layer from the etched feature in the direction of etch propagation.

The substrate may be masked with a suitable pattern defining the areas to be etched.

The support may be in the form of a first electrode, and the apparatus may further comprise a second electrode spaced therefrom.

The apparatus may further comprise means for providing RF energy (inductively and/or capacitively coupled via the electrodes) or microwave energy to a plasma in the chamber for at least part of the cycle. Means may be provided for providing an electrical bias on to the substrate electrode to accelerate ions onto the material surface or film for at least part of the cycle. The apparatus may further comprise means for providing radiation energy into the chamber. The apparatus may further comprise means for controlling the temperature of the substrate or workpiece in the chamber to enhance the deposition of the passivant and/or the etching rate of the substrate and/or the etch rate of the passivant.

The apparatus may further comprise means for substrate rotation for enhancing the process homogeneity across the substrate.

Thus, the means for etching the substrate, means for depositing the passivation layer and means for selectively removing the passivation layer may be associated with a single chamber. This is preferred for reasons of throughput, because there are then no additional substrate handling times. However, alternatively, a separate chamber may be provided for any of the steps as necessary to support the desired means for passivation or passivant removal steps.

Thus, according to a further aspect of the present invention, there is provided an apparatus for performing the method described above, comprising means for etching the material or film with one or more appropriate chemicals, means for depositing a passivation layer on the surfaces of an etched feature, and means for selectively removing the passivation layer from the etched feature in the direction of etch propagation, wherein each of the means for etching, means for depositing the passivation layer and means for selectively removing the passivation layer may be associated with the same or a separate chamber in which the substrate is positioned.

Therefore, not only can each of the means be provided in a single chamber, but one chamber may be provided for each means (providing three chambers in total) or two of the means may be associated with a single chamber with the other means associated with a separate chamber.

According to a further aspect of the present invention, there is provided a method of delivering a vapour into a chamber for etching a substrate positioned therein, the method comprising:

(a) feeding a solution into the chamber by creating droplets on or before entering the chamber;

(b) generating an electrostatic field to electrostatically attract the droplets to the substrate, thereby etching the substrate.

According to a further aspect of the present invention, there is provided a vapour delivering apparatus comprising a dielectric body within which are positioned a plurality of nozzles, each nozzle extending from the back side of the body to the front side, wherein the body is metallized to form a continuous electrical path between the back side and the inside of each nozzle to the tip thereof.

In carrying out the process of this invention any gases employed may be delivered from a delivery system positioned locally to a chamber within which the method is performed. "Locally" means either that the delivery system is associated with that chamber rather than being a central ring mains supply and/or the gas is generated at the point of use. Equally the apparatus of this invention may incorporate a delivery system for the gases used which is positioned locally to the reaction chamber of the apparatus. The local delivery system may utilise molten electrolyte gas generators, particularly for fluorine, nitrogen trifluoride or chlorotrifluoride or inter-halogen gases, such as mixtures thereof. The gas generators contain a solid when cold which allows for safe transportation and storage of the generators. They are able to generate the process gases to high purity and at a reasonable cost and risk. The ability to generate gases or combine gas mixtures, which either require a plasma to produce the reactive species or spontaneously react with the substrate, allows the capability to introduce a process schedule which may only require a plasma for one or other of the process steps in the overall process schedule.

Although the invention has been defined above, it is to be understood that it includes any inventive combination of the features set out above or in the following description.

The invention may be performed in various ways and specific examples thereof will now be described, by way of example, with reference to the accompanying drawings, and in which.

Figure 1:
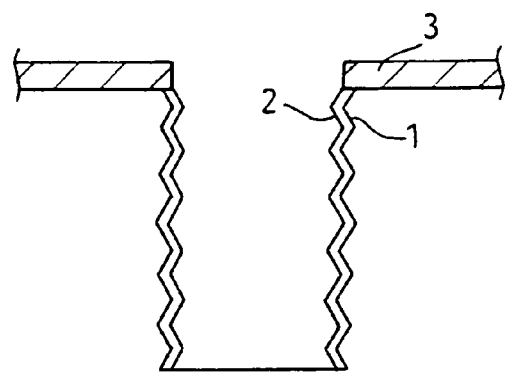
FIG. 1 shows an enlarged schematic cross-sectional view of an anisotropically etched trench in a cyclic etch and passivation method.

Referring to FIG. 1, there is shown a schematic view of a trench formed as described in WO-A-9414187. The process described in that document uses sequential and discrete etch and deposition steps so that after the first etch step the side walls are undercut as shown at 1 and this undercut is then protected by a deposited passivation layer 2. As can be seen from FIG. 1, this arrangement produces a rough sidewall and as the etched steps increase, or indeed the aspect ratio increases, there can be bowing or re-entrant notching in the profile. It is to be noted that the method transfers the pattern made in the mask 3 into the surface of the substrate.

Figure 2:
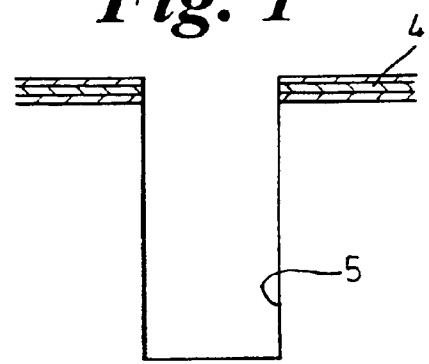
FIG. 2 is an enlarged schematic cross-sectional view of an etched trench formed by way of conventional anisotropic etching.

FIG. 2 shows a schematic view of an etched substrate which has been etched by means of conventional anisotropic etching. Again, a mask 4 is present at the top of the trench 5.

Figure 3:
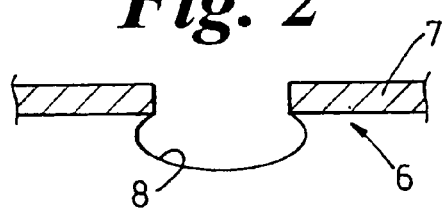
FIG. 3 is an enlarged schematic cross-sectional view showing an isotropic chemical etch process.
Figure 4:
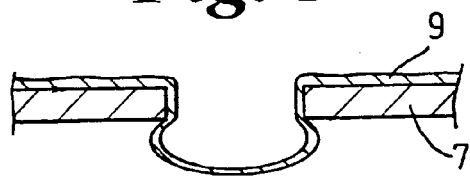
FIG. 4 is an enlarged schematic cross-sectional view showing a deposition of a passivating film.
Figure 5:
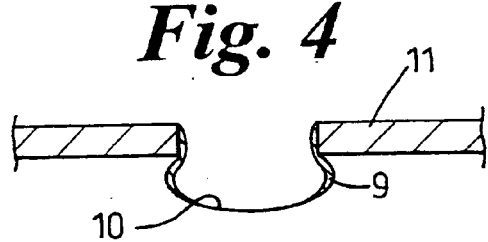
FIG. 5 is an enlarged schematic cross-sectional view showing selective removal of the passivating film from the base of an etched feature.

As mentioned above, a model can be developed for a cyclic anisotropic high rate etching process. Thus, the technique can be applied to enhance etch rates and maintain anisotropy for any material when the three conditions (i) to (iii) mentioned above can be satisfied. This model in use is illustrated schematically in FIGS. 3 to 5. Referring to FIG. 3, there is shown a substrate 6 on which is a masking layer 7 which has been subject to isotropic chemical etching to create a trench 8. As illustrated in FIG. 4, deposition of a passivating film 9 may be carried out to provide protection. The next step proposed by the model is the removal of the passivation material 9 from the base 10 or horizontal surface of the material 11. This allows the etch to proceed in the desired etch direction perpendicular to the plane of the substrate. This model has led to the plasma etching of silicon using $SF_6$ or $NF_3$ based etch chemistry and $C_xH_y$ or $C_xH_yF_z$ passivation chemistry. However, the model would predict that where any of the above conditions (i) to (iii) cannot be satisfied, the method cannot be used significantly to enhance process capability. For example, considering the prior art, this only refers to the enhancement of anisotropic plasma etching by using this method. Therefore, the method is applicable only to those materials which can be etched in a plasma where the isotropic plasma etch component provides the high etch rate means and the sidewall passivation provides the anisotropy means. The use of chemistries which are not plasma etch compatible and indeed simpler non plasma methods are not disclosed. Also by definition, the prior art is thus not applicable to enhance anisotropic etch rates of materials which do not immediately have a high isotropic etch rate component. Materials such as silicon dioxide, silicon carbide or metals such as Au, Pt, NiFe, Fe, NiFeCo (and other metallic magnetic materials) fall into this category. The present invention may thus utilise a non-plasma chemical etch in condition (i) of the model, with either a non plasma (such as radiation enhanced) or plasma enhanced passivation step in condition (ii), and a non plasma (such as radiation enhanced) or plasma step to satisfy condition (iii) of the model. Essentially any of the first two steps at least may be carried out in the absence of a plasma.

The choice of chemistry will depend specifically on the materials being etched. U.S. Pat. Nos. 5,221,366, 5,213,621 and 5,213,622 disclose the use of diketones, ketoimines, halogenated-carboxylic acid, acetic acid and formic acid chemistries to etch various metals in the vapor phase. Such chemistries (and extensions including hexafluoro-2,4-pentanedione and other fluorinated acetyl-acetone groups) may be used for the vapor etching of various metallic and magnetic materials. The prior art discloses the use of elevated temperatures to enhance the etching; indeed in some cases several hundred degrees are necessary in order to achieve any etching. The process of the present invention can be operated at pressures above atmosphere and/or at elevated temperatures (depending upon temperature restrictions imposed by the device being etched) to enhance the etch rate for such metallic and magnetic materials.

In a specific embodiment, the invention applies this to oxide etching by:

(i) the use of anhydrous HF based chemicals to etch the oxide;

(ii) depositing passivation (preferably using $C_xF_y$, either with or without plasma enhancement); and (iii) the use of either directional plasma generated ion bombardment or directional non-plasma irradiation means to remove the passivation.

Figure 6:
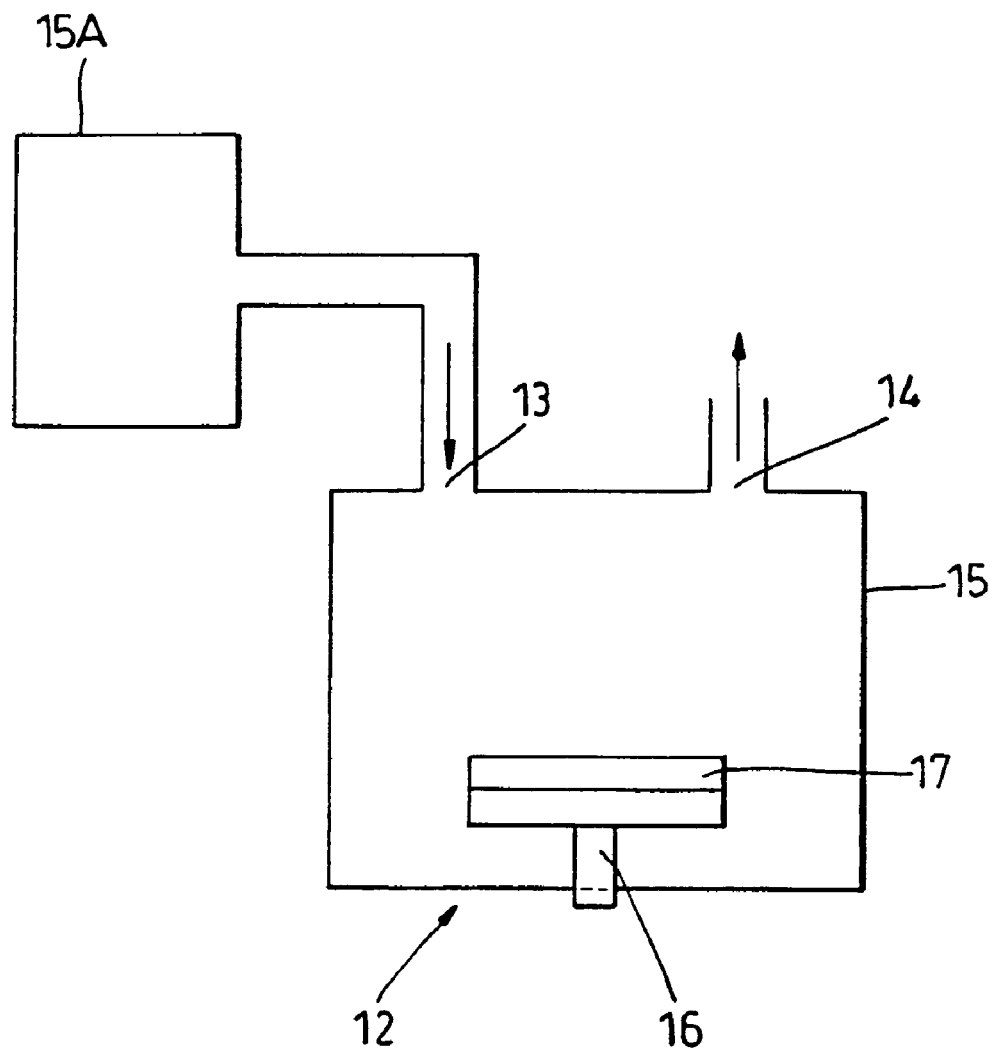
FIG. 6 shows a diagrammatic view of an apparatus for carrying out the etching step of the present invention.

FIG. 6 shows one embodiment of a specific apparatus used in the invention shown generally at 12 for carrying out chemical etching with HF based chemistry. The anhydrous HF and other chemicals may enter at inlet port 13 and exit at outlet port 14 which are connected to a chamber 15. The chamber 15 further comprises therein an electrode 16 on which is positioned an oxide (eg silicon dioxide) substrate 17. The chamber 15 is at a pressure of about 760–500 Torr and the total gas flow is between 15 and 30 SLM. In use, the anhydrous HF, together with either an alcohol or $H_2O$ and $N_2$ carrier gas is passed into the chamber 15 through inlet port 13 and etches substrate 17 to form an etched feature therein. Alternative apparatus for carrying out this step is disclosed in DE 19704454 and DE 4317274.

As shown in FIG. 6, the chamber 15 can be supplied with the process gases through the inlet port 13 from a local delivery system 15A which is able to generate the required gas or gases from available molten electrolyte gas generators.

Figure 7A:
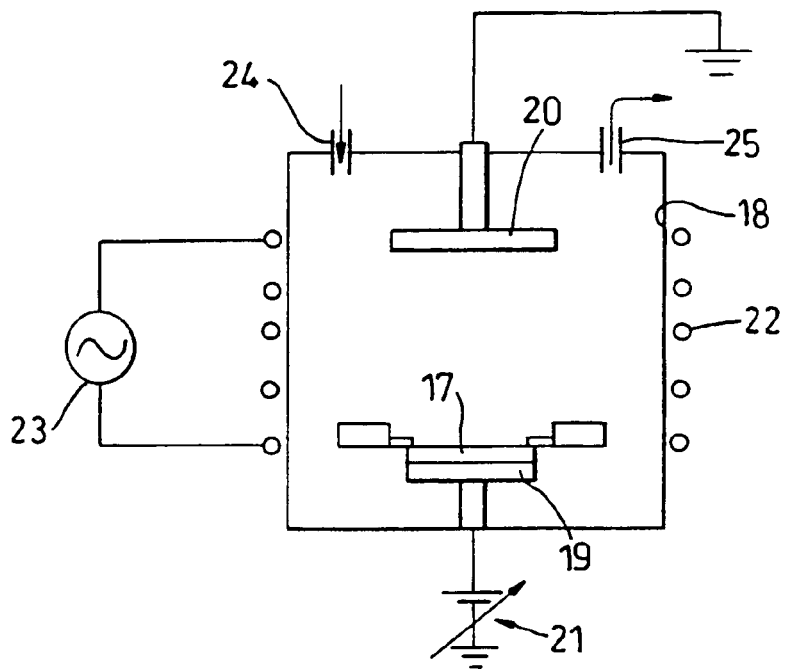
FIGS. 7A and 7B show diagrammatic views of an apparatus for carrying out the final two steps of the process or all of the process steps of the present invention.
Figure 7B:
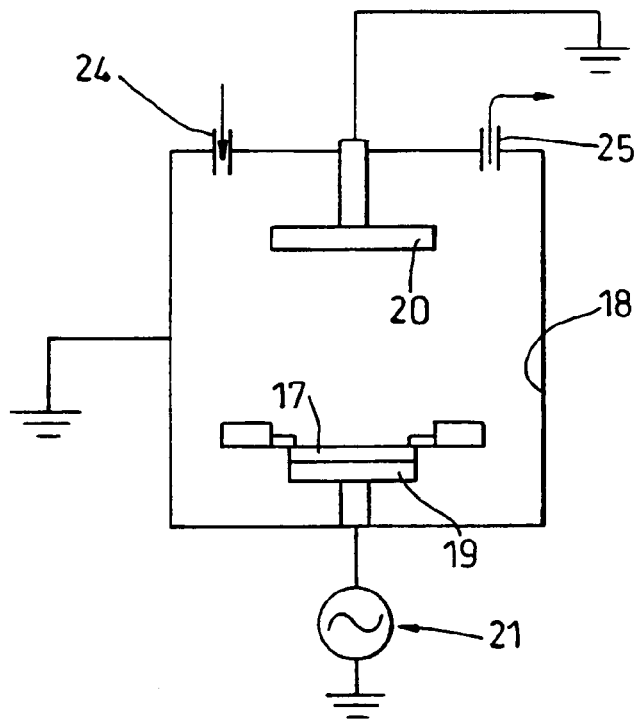

FIGS. 7A and 7B show alternative schematic apparatuses which can be used either for all three steps of the invention, or for the second and third steps (i.e. the passivation and directional removal of the passivation layer). FIG. 7A illustrates a vacuum chamber 18 incorporating a support electrode 19 for receiving the oxide substrate 17 which may be in the form of a semiconductor wafer. Also shown is a further spaced electrode 20.

The chamber 18 is surrounded by a coil 22 fed by an RF source 23 which is used to induce a plasma in the chamber 11 between the electrodes 19 and 20, for example when this is required in any of the plasma based steps of the invention. Bias means 21 is associated with electrode 19. The chamber is provided with a gas inlet port 24 through which deposition or etch gases can be introduced and an exhaust port 25 for the removal of gaseous process products and any excess process gas.

The bias means 21 shown in FIGS. 7A and 7B bias power onto the substrate electrode to achieve step 3. Bias is typically capacitatively coupled rf, but dc is possible when conducting substrates are used.

FIG. 7B shows a schematic view of an alternative apparatus to that shown in FIG. 7A. The apparatus works in a similar way to that shown in FIG. 7A and like reference numerals show like parts. The difference between the apparatus shown in FIG. 7B and that shown in FIG. 7A is the mode of RF energy (inductive and capacitive) coupled into the plasma for any of the plasma based steps. FIG. 7A illustrates an inductive method of coupling rf power and FIG. 7B shows a capacitive method for applying the rf power. Although they are not presented, other types of plasma source such as MORI, ECR and the like can equally be used. Thus, in FIG. 7B, there is shown a first RF source and impedance matching unit 21 acting on electrode 19. The first RF power and matching unit may act on the top electrode, and an additional second RF source and matching unit may act on the lower electrode to act as the biasing supply.

For the second step of the invention, that is the deposition of the passivation layer, the ideal operation conditions are as follows. A low pressure plasma, at a pressure ranging from several hundred Torr down to several mTorr, depending upon the type of reactor, is present in the chamber 18. A fluorocarbon gas source such as $C_4F_8$, possibly in a helium or argon carrier gas, is passed into the chamber 18 through inlet port 24 and is polymer deposited on the surfaces of the substrate 17.

The third step of the invention, that is the selective removal of the passivation layer, is also carried out in the chamber 18 illustrated in FIGS. 7A and 7B. A low pressure plasma, preferably less than several hundred mTorr and ideally less than or equal to 10 mTorr depending upon the type of reactor, is used, and the total gas flow is in the range 5–100 sccm when argon is used for the selective removal.

Figure 8A:
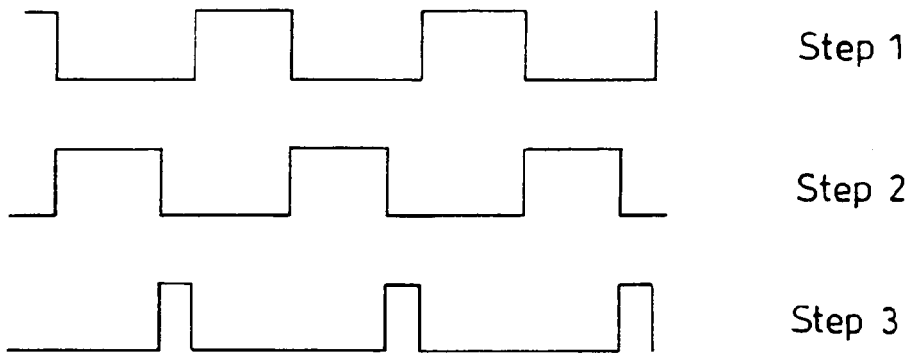
FIGS. 8A to 8C show diagrammatically various different step sequences of the present invention.
Figure 8B:
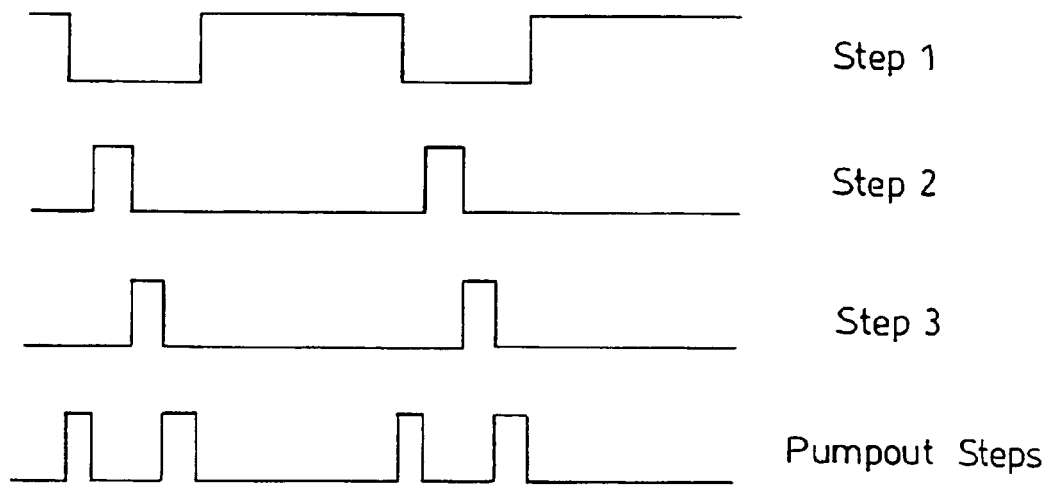
Figure 8C:
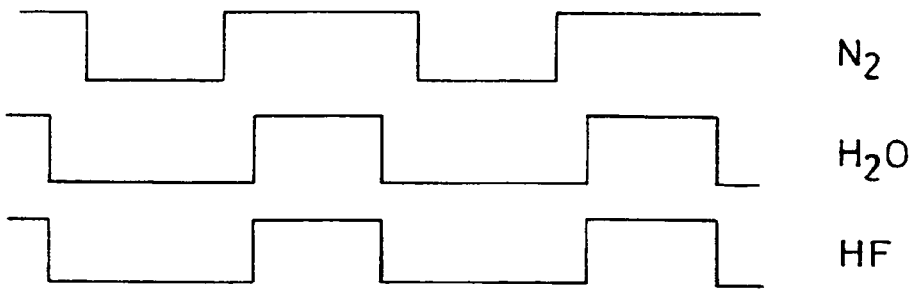

FIG. 8A shows the ideal sequencing of the chemical/gases only into the process chamber. Step 1 refers to the flow of the etchant chemicals into the chamber, step 2 refers to the passing of a passivation gas into the chamber and step 3 refers to the passing of the plasma etch gas into the chamber. However, it has been found practically that, as the flow rates and operational pressures differ greatly between the first step and the other two steps, a pump out and pressure stabilization type is often necessary. This leads to the sequence shown in FIG. 8B. Although the sequence shows a single chemical or gas flow, it is to be understood that more than one chemical or gas may be used as necessary. As an example, FIG. 8C shows the detailed breakdown of the sequence of step 1 gases only, highlighting the use of $N_2$ carrier gas as a purging gas as well.

Figure 9A:
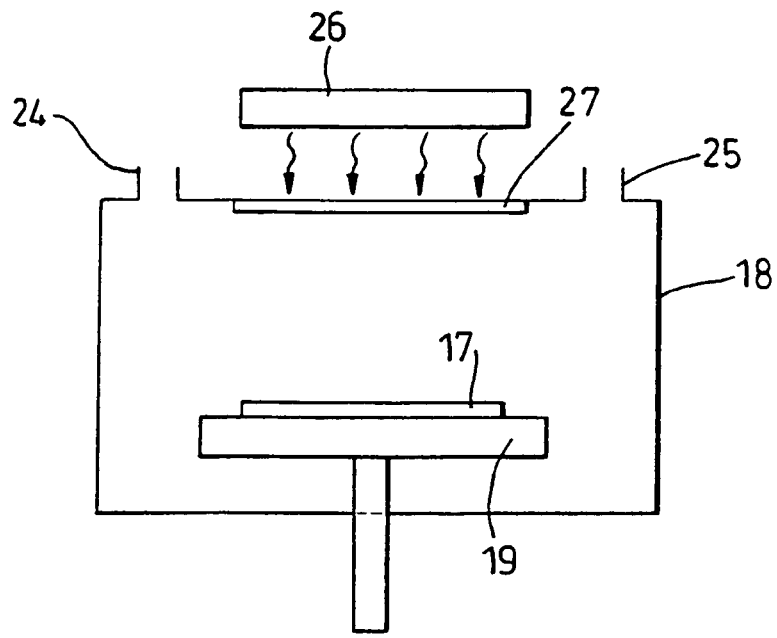
FIGS. 9A and 9B show diagrammatically a view of an alternative apparatus for carrying out all the steps or the final two steps of the process of the present invention.

This drawback of different operational pressures and conditions can be overcome by another embodiment. This is shown diagrammatically in FIG. 9A. This shows an apparatus which can be used for deposition of a polymer for step 2 by means of irradiation of the precursor gas which passes over the substrate 17 after entering into the reactor through port 24 and exiting the reactor via port 25. It is preferred to cool the wafer support electrode 19 so as to enhance polymer condensation onto the substrate. The radiation (including either UV or IR) is supplied by external means 26 including laser excitation means such as an excimer laser and enters into the chamber by a suitable window 27. Radiation enhanced polymerisation methods are well known to those skilled in the art. The process regime in terms of operational pressure can be very similar to that required for the chemical etch step, that is close to atmospheric pressure.

Figure 9B:
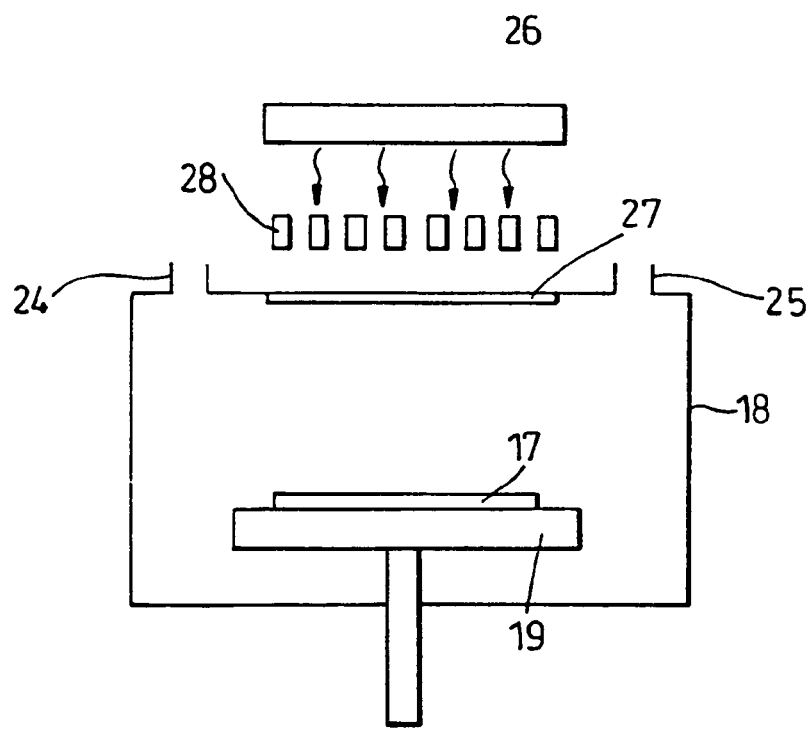
Figure 10A:
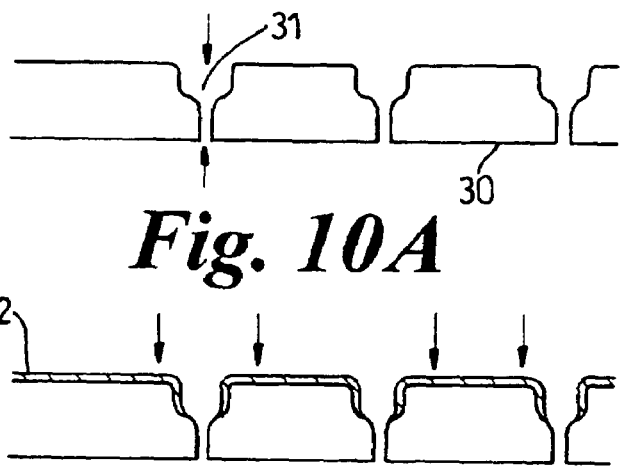
FIGS. 10A to 10C and 11 show the steps of production of a multiple nozzle showerhead of the invention and a resulting product respectively.
Figure 10B:
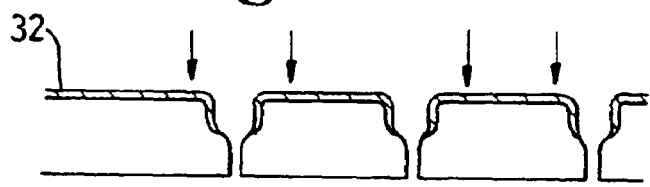
Figure 10C:
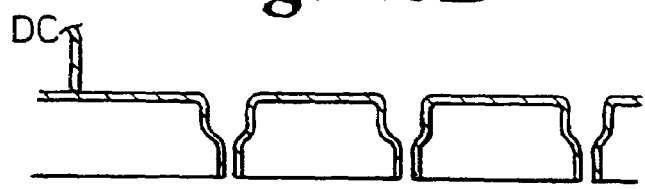
Figure 11:
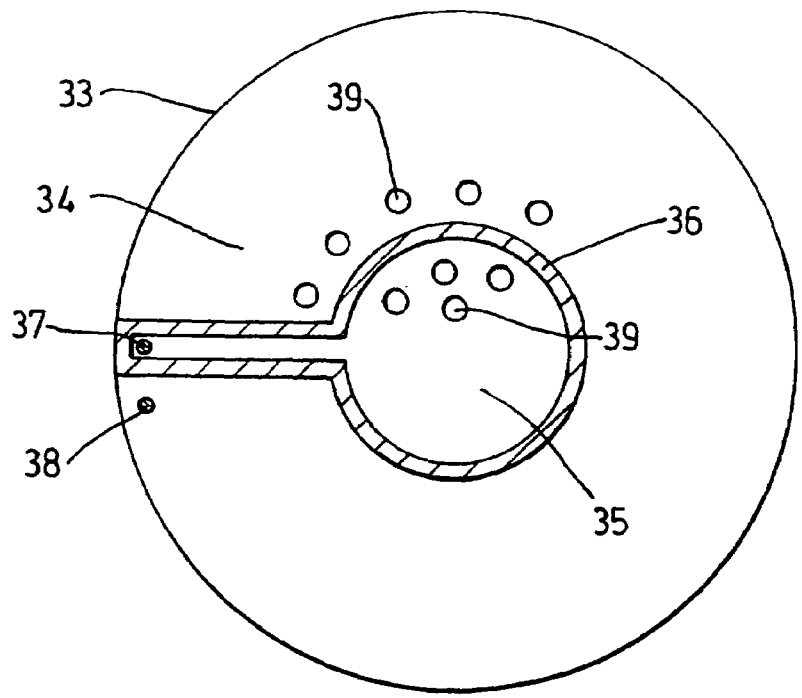

FIG. 9B shows diagrammatically an apparatus for achieving step 3 by using collimated surface irradiation. As this will be without a plasma, the same benefits of similarity of operational window with step 1 can be obtained. The Fgure shows the substrate 17 resting on the wafer support electrode 19. The radiation is supplied by external means 26 and enters into the chamber by a suitable window 27 via a collimator 28. Alternatively, U.S. Pat. No. 4,529,475 discloses the use of two irradiation sources perpendicular to each other, one of which may be used for the deposition (step (ii)) whilst the other may be used for the removal of the polymer (step (iii)).

Vapor Delivery Methods:

Electrostatic spray delivery techniques may be used as follows:

a) the solution is fed into the chamber (for example by means of an MFC or syringe or constant static pressure feed pump) creating a stream of droplets; and b) an electrostatic field is generated to electrostatically attract the droplets to the substrate.

Droplets are provided with a positive or negative DC charge by means of a high voltage power supply connected to the droplet inlet point into the chamber. The substrate electrode is grounded with respect to the DC supply. At the droplet inlet, typical electrostatic field strengths in the range 2 to 30 kV/mm are required. At these intensities, a corona discharge is created at the inlet point which helps to charge and atomize the droplets and direct the resultant spray towards the grounded substrate electrode. Charging of the droplets can also increase the process reaction rate. Solution conductivity can also influence the droplet size. For example, ethanoic acid addition results in increased electrical conductivity and thereby results in a finer droplet spray.

Ideally the outlet consists of a nozzle with less than or equal to 1 mm inner diameter. Practically, in order to get good uniformity across relatively large areas, one of the following methods may be needed:

a) raster scanning of one of more nozzles (which only allow partial spray coverage over the substrate) and/or appropriate substrate rotation;

b) multiple nozzles to allow full substrate coverage with possible substrate rotation (see below).

Multiple Nozzle Showerhead to Allow Full Substrate Coverage

Current methods and prior art refer to the use of one or more nozzles to introduce the vapor. The nozzles must be conducting to allow electrostatic charging of the tip. As the tip dimension is small (<1 mm), electric field enhancement occurs. This enhancement increases the electric field at the tip from in the range of 2 to 30 kV/mm by several orders of magnitude. At these high fields, a local corona discharge will occur, which assists in the creation of a fine charged droplet spray which is attracted towards the DC grounded substrate electrode. Practically it is difficult to use large numbers of nozzles to cover large area substrate processing.

This aspect of the invention relates to the design of a showerhead which allows both uniform vapor distribution as well as maintaining high electric field enhancement factors.

FIG. 10 shows the fabrication steps for the manufacture of the showerhead 29, namely:—

A. A dielectric plate 30 (such as quartz, glass or pyrex) is drilled from the back side with tapering holes 31 (or a number of superimposed holes with reducing diameter) to create the required nozzle shape. Small size holes (for example up to 1 mm) are drilled from the front, followed by larger holes drilled from the back side. The number of holes and separation chosen depends on the required electric field enhancement vapor flow rate and pressure.

B. The back side 32 of the plate is then metallized to form a continuous electrical path between the back surface and the inside of each of the nozzles up to the tip of each nozzle.

C. Electrical connections are then made to the metallized section on the back side for the dc power supply.

FIG. 11 shows a variation where different areas of the showerhead 33 can be connected to different power supplies with either the same potential, or different potentials to create a field gradient across the nozzle tip showerhead. This may be used to tailor the vapor distribution across the showerhead. The showerhead is divided into zones 34,35 by a non-metallised section 36, with separate DC contacts 37,38 being made to each zone. The nozzle holes 39 (partially shown only) will uniformly cover the showerhead 33.

The invention claimed is:

1. A method of treating a substrate material or film present on the material surface comprising repeatedly performing an etching process cycle, wherein each etching process cycle increases a depth of an etched feature in the material or film, and wherein each etching process cycle includes performing the following sequential steps:

(a) etching the material or film to increase the depth of the etched feature;

(b) depositing or forming a passivation layer on the surfaces of the etched feature; and (c) partially and selectively removing the passivation layer from the surfaces of the etched feature in order that the etching of subsequent etching process cycles proceeds in a direction substantially perpendicular to the material or film surface, wherein at least one of steps (a) or (b) is performed in the absence of a plasma, and wherein step (c) of each cycle is performed separately from step (a) of each next cycle.

2. A method according to claim 1, wherein step (a) is performed with one or more appropriate chemicals in the absence of a plasma.

3. A method according to claim 1, wherein the other of steps (a) and (b) is performed in the presence of a plasma.

4. A method according to claim 1, wherein the material surface has previously had a mask pattern defined thereon.

5. A method according to claim 1, wherein the material or film is a dielectric.

6. A method according to claim 5, wherein the material or film is an oxide, preferably of silicon, quartz, glass, pyrex, $SiO_2$ deposited by CVD, or $SiO_2$ grown by thermal, plasma or other means to deposit or grow the oxide.

7. A method according to claim 1, wherein the material or film is etched with HF.

8. A method according to claim 1, wherein $H_2O$ and/or an alcohol is present in step (a).

9. A method according to claim 1, wherein the material or film is a semiconductor, preferably a Si, SiGe or Ge semiconductor.

10. A method according to claim 9, wherein the material or film is etched with HF, $HNO_3$ and $CH_3COOH$, or with a halogen containing compound, preferably an inter-halogen gas comprising halogen components only.

11. A method according to claim 1, wherein the material or film is a conductor, preferably an Au or Pt conductor.

12. A method according to claim 11, wherein the material or film is etched using aqua regia.

13. A method according to claim 1, wherein $N_2$ or other inert gas is present in step (a) and/or is used as a purging gas between the steps of the method.

14. A method according to claim 1, wherein the passivation layer is formed on a surface that is resistant to chemical etch.

15. A method according to claim 1, wherein the passivation layer is deposited using a polymer.

16. A method according to claim 15, wherein the polymer is a per-fluoro polymer of formula $n(C_xF_y)$, where x and y are suitable values.

17. A method according to claim 1, wherein, when a plasma is not present in step (b), a photo-enhanced polymerization process in used in the deposition of the passivation layer.

18. A method according to claim 1, wherein the selective removal of the passivation layer is carried out by surface irradiation.

19. A method according to claim 18, wherein the irradiation is thermal heating of either the front and/or the rear surface of the material or film to provide thermolytic decomposition, or is provided by a light source of the front of the material or film resulting in photolytic decomposition, or wherein the irradiation source is an excimer laser.

20. A method according to claim 18, wherein the irradiation is directional or collimated parallel to the direction of etch front propagation.

21. A method according to claim 18, wherein the surface irradiation is a plasma, wherein the ion energy in the plasma is preferably greater than 10 eV.

22. A method according to claim 21, wherein the plasma comprises a precursor gas or mixture of precursor gases.

23. A method according to claim 22, wherein the precursor gas comprises an inert gas which is capable of physically removing the passivation layer and/or a gas which is capable of physically removing the passivation layer with chemical enhancement.

24. A method according to claim 22, wherein the precursor gas comprises an etchant chemical used in step (a) or a material used for depositing the passivation layer in step (b).

25. A method according to claim 1, wherein any gases employed are delivered from a point of use delivery system positioned locally to a chamber within which the method is performed.

26. A method according to claim 1 for treating a substrate material or film formed from metallic and magnetic materials, wherein the etching step (a) is operated at pressures above atmosphere and/or at elevated temperatures using as etchant materials any one or more of diketones, ketoimines, halogenated-carboxylic acid, acetic acid, and formic acid chemistries and extensions including hexafluoro-2,4-pentanedione and other fluorinmated acetyl-acetone groups.

* * * * *